(12) United States Patent
Jaax et al.

(10) Patent No.: US 8,515,541 B1
(45) Date of Patent: Aug. 20, 2013

(54) METHODS AND SYSTEMS FOR TREATING POST-STROKE DISORDERS

(75) Inventors: Kristen N. Jaax, Saugus, CA (US); Todd K. Whitehurst, Santa Clarita, CA (US); Rafael Carbunaru, Studio City, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1529 days.

(21) Appl. No.: 11/317,465

(22) Filed: Dec. 22, 2005

Related U.S. Application Data (60) Provisional application No. 60/638,946, filed on Dec. 22, 2004.

(51) Int. Cl.
*A61N 1/36* (2006.01)

(52) U.S. Cl.
USPC .............................. 607/45; 607/46; 607/116

(58) Field of Classification Search
USPC .................. 607/45, 48, 59, 115, 116, 139, 46
See application file for complete search history.

(56) References Cited

U.S. PATENT DOCUMENTS

| | | | |
|---|---|---|---|
| 3,760,984 A | 9/1973 | Theeuwes | |
| 3,845,770 A | 11/1974 | Theeuwes et al. | |
| 3,916,899 A | 11/1975 | Theeuwes et al. | |
| 3,923,426 A | 12/1975 | Theeuwes | |
| 3,987,790 A | 10/1976 | Eckenhoff et al. | |
| 3,995,631 A | 12/1976 | Higuchi et al. | |
| 4,016,880 A | 4/1977 | Theeuwes et al. | |
| 4,036,228 A | 7/1977 | Theeuwes | |
| 4,111,202 A | 9/1978 | Theeuwes | |
| 4,111,203 A | 9/1978 | Theeuwes | |
| 4,203,440 A | 5/1980 | Theeuwes | |
| 4,203,442 A | 5/1980 | Michaels | |
| 4,210,139 A | 7/1980 | Higuchi | |
| 4,327,725 A | 5/1982 | Cortese et al. | |

(Continued)

FOREIGN PATENT DOCUMENTS

| | | |
|---|---|---|
| WO | WO 01/82398 A1 | 1/2001 |
| WO | WO 02/072194 A2 | 9/2002 |
| WO | WO 03/005465 A1 | 1/2003 |
| WO | WO03066154 * | 8/2003 |

OTHER PUBLICATIONS

Angelo Franzini; Reversal of Thalamic Hand Syndrome by Long-Term Motor Cortex Stimulation; Journal of Neurosurgery; Nov. 2000; 873-875; vol. 93 No. 5.

(Continued)

*Primary Examiner* — Carl H Layno
*Assistant Examiner* — Jennifer Ghand
(74) *Attorney, Agent, or Firm* — Vista IP Law Group LLP (57) ABSTRACT

Methods of treating a post-stroke disorder include applying at least one stimulus to a stimulation site within a patient with an implanted stimulator in accordance with one or more stimulation parameters. The stimulation site may include, for example, at least one or more of a motor cortex, thalamus, cerebellum, basal ganglia, globus pallidus, and periaqueductal gray. Systems for treating a post-stroke disorder include an implantable stimulator configured to apply at least one stimulus to a stimulation site within a patient in accordance with one or more stimulation parameters. The stimulation site may include, for example, at least one or more of a motor cortex, thalamus, cerebellum, basal ganglia, globus pallidus, and periaqueductal gray.

4 Claims, 9 Drawing Sheets

(56) References Cited

U.S. PATENT DOCUMENTS

| | | | |
|---|---|---|---|
| 4,360,019 A | 11/1982 | Portner et al. | |
| 4,487,603 A | 12/1984 | Harris | |
| 4,562,751 A | 1/1986 | Nason et al. | |
| 4,627,850 A | 12/1986 | Deters et al. | |
| 4,678,408 A | 7/1987 | Nason et al. | |
| 4,685,903 A | 8/1987 | Cable et al. | |
| 4,692,147 A | 9/1987 | Duggan | |
| 4,725,852 A | 2/1988 | Gamblin et al. | |
| 4,865,845 A | 9/1989 | Eckenhoff et al. | |
| 5,057,318 A | 10/1991 | Magruder et al. | |
| 5,059,423 A | 10/1991 | Magruder et al. | |
| 5,080,653 A | 1/1992 | Voss et al. | |
| 5,097,122 A | 3/1992 | Colman et al. | |
| 5,112,614 A | 5/1992 | Magruder et al. | |
| 5,137,727 A | 8/1992 | Eckenhoff | |
| 5,193,539 A | 3/1993 | Schulman et al. | |
| 5,193,540 A | 3/1993 | Schulman et al. | |
| 5,234,692 A | 8/1993 | Magruder et al. | |
| 5,234,693 A | 8/1993 | Magruder et al. | |
| 5,312,439 A | 5/1994 | Loeb | |
| 5,501,703 A | 3/1996 | Holsheimer | |
| 5,713,922 A * | 2/1998 | King | 607/2 |
| 5,728,396 A | 3/1998 | Peery et al. | |
| 5,938,688 A | 8/1999 | Schiff | |
| 6,016,449 A | 1/2000 | Fischell et al. | |
| 6,051,017 A | 4/2000 | Loeb et al. | |
| 6,066,163 A * | 5/2000 | John | 607/45 |
| 6,094,598 A * | 7/2000 | Elsberry et al. | 607/116 |
| 6,164,284 A | 12/2000 | Schulman et al. | |
| 6,185,452 B1 | 2/2001 | Schulman et al. | |
| 6,208,894 B1 | 3/2001 | Schulman et al. | |
| 6,219,580 B1 | 4/2001 | Faltys et al. | |
| 6,272,382 B1 | 8/2001 | Faltys et al. | |
| 6,280,873 B1 | 8/2001 | Tsukamoto | |
| 6,308,101 B1 | 10/2001 | Faltys et al. | |
| 6,356,784 B1 * | 3/2002 | Lozano et al. | 607/2 |
| 6,368,315 B1 | 4/2002 | Gillis et al. | |
| 6,381,496 B1 | 4/2002 | Meadows et al. | |
| 6,405,079 B1 | 6/2002 | Ansarinia | |
| 6,458,171 B1 | 10/2002 | Tsukamoto | |
| 6,484,059 B2 | 11/2002 | Gielen | |
| 6,487,446 B1 | 11/2002 | Hill et al. | |
| 6,516,227 B1 | 2/2003 | Meadows et al. | |
| 6,539,263 B1 | 3/2003 | Schiff et al. | |
| 6,553,263 B1 | 4/2003 | Meadows et al. | |
| 6,620,151 B2 | 9/2003 | Blischak et al. | |
| 6,666,845 B2 | 12/2003 | Hooper et al. | |
| 6,740,072 B2 | 5/2004 | Starkweather et al. | |
| 6,760,626 B1 | 7/2004 | Boveja | |
| 6,770,067 B2 | 8/2004 | Lorenzen et al. | |
| 6,959,215 B2 | 10/2005 | Gliner et al. | |
| 7,013,177 B1 * | 3/2006 | Whitehurst et al. | 607/46 |
| 2001/0046625 A1 | 11/2001 | Ruth, II et al. | |
| 2001/0053476 A1 | 12/2001 | Ruth et al. | |
| 2002/0091419 A1 * | 7/2002 | Firlik et al. | 607/45 |
| 2005/0065574 A1 * | 3/2005 | Rezai | 607/45 |
| 2005/0154435 A1 | 7/2005 | Stern et al. | |
| 2006/0004422 A1 * | 1/2006 | De Ridder | 607/45 |
| 2006/0155348 A1 * | 7/2006 | deCharms | 607/89 |

OTHER PUBLICATIONS

Yoichi Katayama; Control of Post-Stroke Movement Disorders Using Chronic Motor Cortex Stimulation; Acta Neurochir Suppl.; 2002; 89-92; vol. 79.

Yoichi Katayama; Motor Cortex Stimulation for Post-Stroke Pain: Comparison of Spinal Cord and Thalmic Stimulation; Journal; 2001; 183-186; vol. 77; No. (1-4).

Dipankar Nandi; Pen-ventricular Grey Stimulation Versus Motor Cortex Stimulation for Post Stroke Neuropathic Pain; 2002; 557-561; vol. 9; No. 5.

Clemens Sommer; Exogenous Brain-Derived Neurotrophic Factor Prevents Postischemic Downregulation of [3H] Muscimol Binding to GABA(a) Receptors in the Cortical Penumbra; 2003.

Tung-Han Tsai; Gene Treatment of Cerebral Stroke by rAAV Vector Delivering IL-Ira in a Rat Model; Feb. 3, 2003; 803-807; vol. 14; No. 6.

Midori A. Yenari; Gene Therapy and Hypothermia for Stroke Treatment; Ann NY Acad Sci.; 2003; 54-68.

Z. Zheng; Stroke: Molecular Mechanisms and Potential Targets for Treatment; Current Molecular Medicine; 2003; 361-372; vol. 3.

* cited by examiner

METHODS AND SYSTEMS FOR TREATING POST-STROKE DISORDERS

RELATED APPLICATIONS

The present application claims the priority under 35 U.S.C. §119(e) of previous U.S. Provisional Patent Application No. 60/638,946, filed Dec. 22, 2004, which is incorporated herein by reference in its entirety.

BACKGROUND

Stroke is the third leading cause of death and the leading cause of adult disability in the United States. Approximately 400,000 individuals in the U.S. suffer a stroke every year. For those who survive, it is a major cause of long-term disability. It is estimated that only ten percent of those who survive a stroke are able to return to their previous activities without significant impairment. Forty percent of all individuals who suffer an acute stroke are disabled to the extent that they require special assistance. Of these, ten percent need institutional care.

Stroke is classified by its cause into two main types: ischemic and hemorrhagic. In ischemic stroke, which occurs in approximately ninety percent of strokes, a blood vessel becomes occluded, and the blood supply to part of the brain is totally or partially blocked. Ischemic stroke is usually caused by atherosclerosis (fatty lumps in the artery wall), embolism (obstruction of blood vessels by blood clots from elsewhere in the body), or microangiopathy (small artery disease, the occlusion of small cerebral vessels).

The middle cerebral artery (MCA) is the vessel most commonly responsible for ischemic stroke. Sites within the brain affected by occlusion of the MCA include the motor cortex, sensory cortex, and Wernicke's area. Resulting functional deficits include sensory deficits, aphasia, and paralysis.

Hemorrhagic stroke, on the other hand, occurs when a blood vessel in the brain bursts, spilling blood into the spaces surrounding the brain cells. Hemorrhagic strokes generally carry a greater risk of death and permanent disability than ischemic strokes. Causes of hemorrhagic stroke include hypertension, cerebral aneurysms, cerebral arteriosclerosis, head injury, congophilic angiopathy, congenital artery defects, and prematurity.

Physical disabilities that can result from stroke include, but are not limited to, paralysis, numbness, pressure sores, pneumonia, incontinence, coma, apraxia (inability to perform learned movements), difficulties carrying out daily activities, appetite loss, vision loss, and pain. Emotional problems resulting from stroke can result from direct damage to emotional centers in the brain or from frustration and difficulty adapting to new limitations. Post-stroke emotional disorders include anxiety, panic attacks, flat affect (failure to express emotions), mania, apathy, and psychosis.

It is estimated that thirty to fifty percent of stroke survivors suffer post-stroke depression, which is characterized by lethargy, irritability, sleep disturbances, lowered self esteem, and withdrawal. Post-stroke depression is often treated with antidepressant drugs, which can present a risk of abuse or addiction.

Emotional lability, another condition associated with stroke, occurs in about twenty percent of stroke patients and causes a patient to switch quickly between emotional highs and lows and to express emotions inappropriately (e.g., an excess of laughing or crying with little or no provocation). While these expressions of emotion usually correspond to the patient's actual emotions, a more severe form of emotional lability causes patients to laugh and cry pathologically, without regard to context or emotion. Some patients show the opposite of what they feel, (e.g., crying when they are happy).

Cognitive deficits resulting from stroke include perceptual disorders, speech problems, dementia, and problems with attention and memory. A stroke sufferer may be perpetually unaware of his or her own disabilities or even the fact that he or she has suffered a stroke.

A number of treatments are available to prevent stroke. However, the options for treating post-stroke disorders and for functional recovery following stroke are limited.

SUMMARY

Methods of treating a post-stroke disorder include applying at least one stimulus to a stimulation site within a patient with an implanted stimulator in accordance with one or more stimulation parameters. The stimulation site may include, for example, at least one or more of a motor cortex, thalamus, cerebellum, basal ganglia, globus pallidus, and periaqueductal gray.

Systems for treating a post-stroke disorder include an implantable stimulator configured to apply at least one stimulus to a stimulation site within a patient in accordance with one or more stimulation parameters. The stimulation site may include, for example, at least one or more of a motor cortex, thalamus, cerebellum, basal ganglia, globus pallidus, and periaqueductal gray.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

DETAILED DESCRIPTION

Methods and systems for treating post-stroke disorders are described herein. An implanted stimulator is configured to apply at least one stimulus to a stimulation site within a patient in accordance with one or more stimulation parameters. The stimulus is configured to treat one or more post-stroke disorders and may include electrical stimulation, drug stimulation, chemical stimulation, thermal stimulation, electromagnetic stimulation, mechanical stimulation, and/or any other suitable stimulation. The stimulation sites that may be stimulated may include at least one or more of a motor cortex, thalamus, cerebellum, basal ganglia, globus pallidus, and periaqueductal gray.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1A:
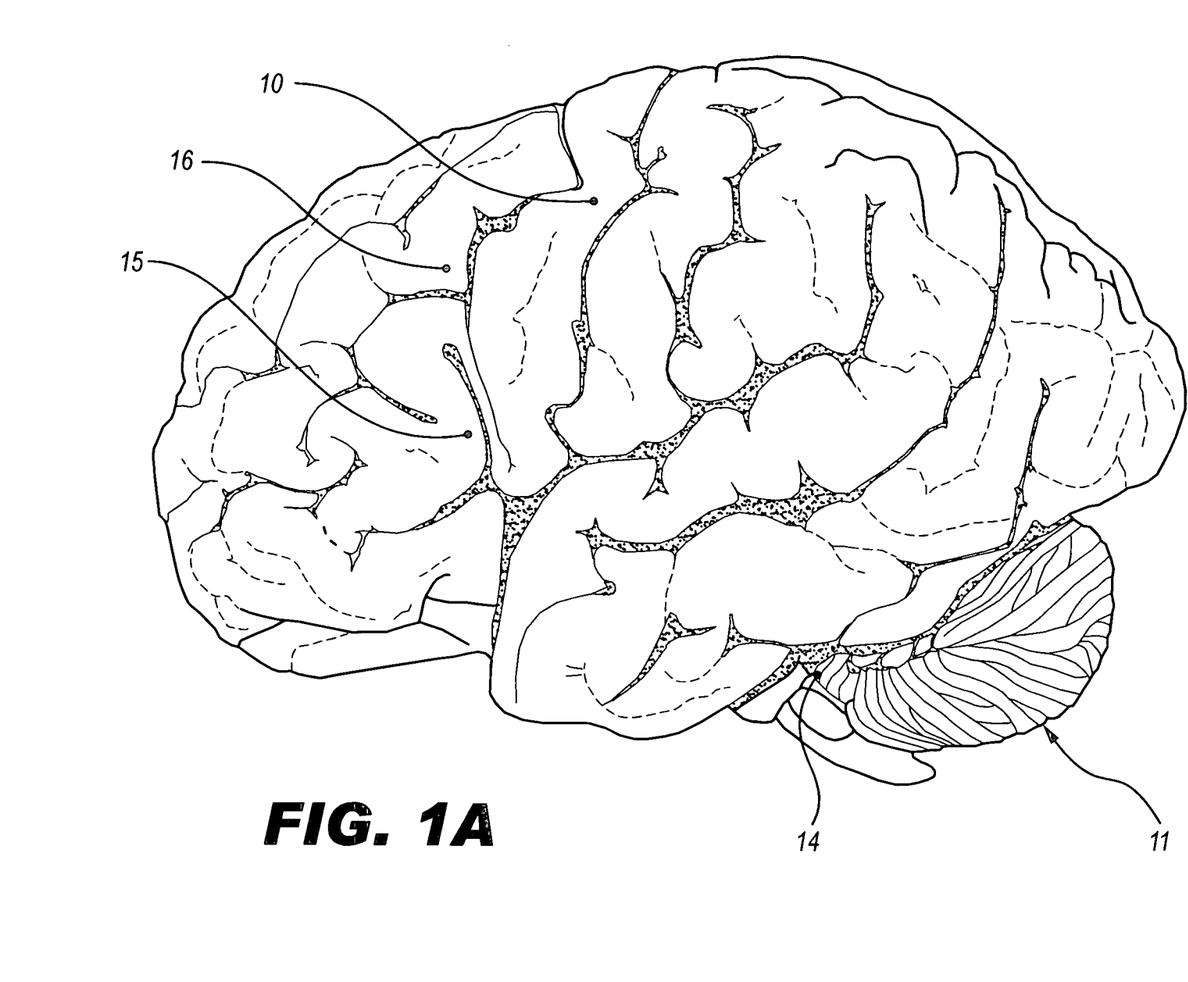
FIG. 1A depicts the lateral surface of the brain.

FIG. 1A depicts the lateral surface of the brain. As shown in FIG. 1A, the primary motor cortex (10) is located on the lateral surface of the brain. The primary motor cortex (10) is the cortical area that influences motor movements. Also shown in FIG. 1A are the premotor cortex (15) and the supplementary motor cortex (16). These structures are also involved in controlling motor movements.

FIG. 1A also shows the cerebellum (11) and periaqueductal gray (14). The cerebellum (11) is located in the back of the head and is responsible for the coordination of movement and balance. The cerebellum (11) includes the superior, middle and/or inferior cerebellar peduncles (not shown). The periaqueductal gray (14) plays a role in the suppression of pain and in defensive behavior.

Figure 1B:
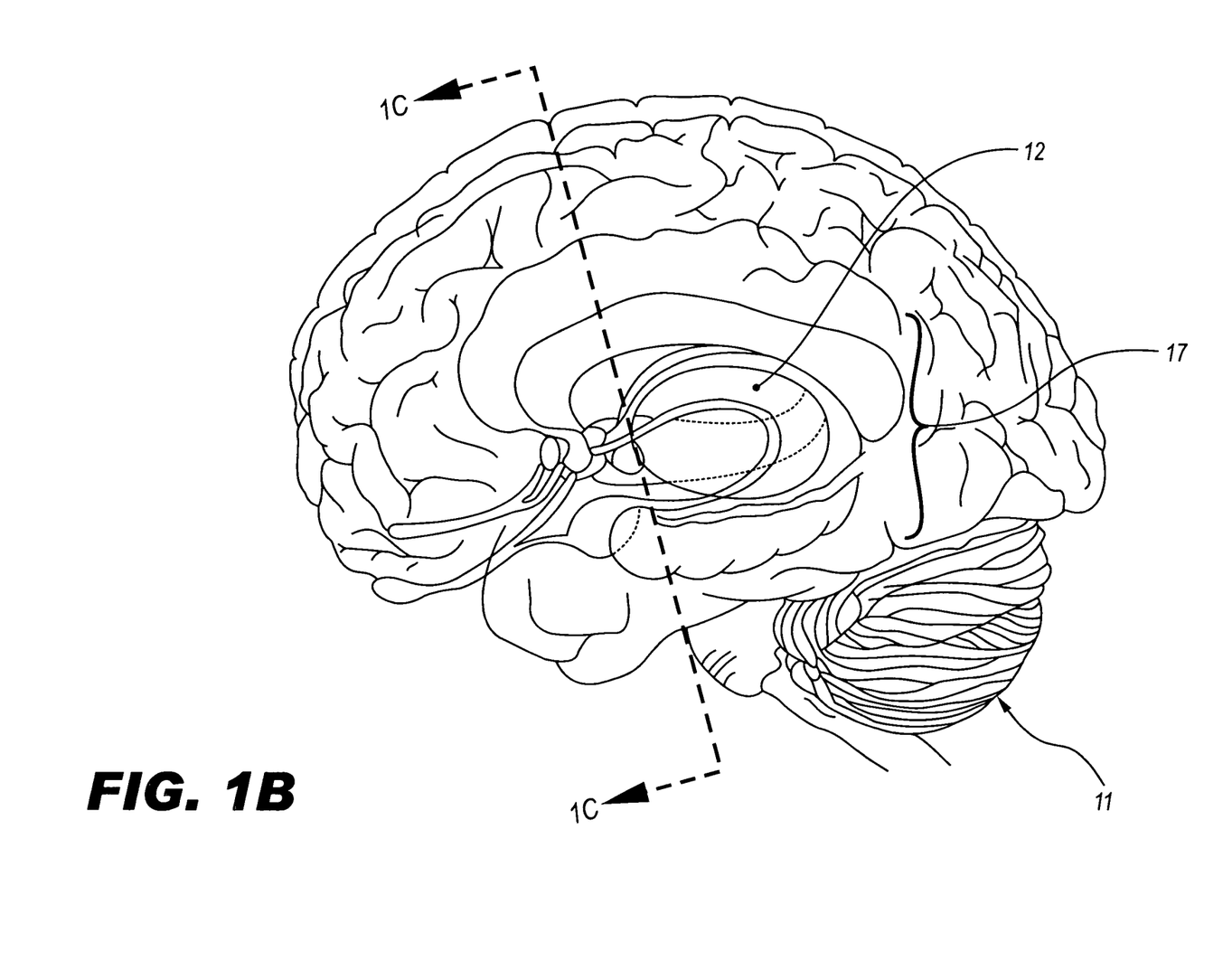
FIG. 1B is a perspective lateral view of the brain.

FIG. 1B is a perspective lateral view of the brain. FIG. 1B shows the thalamus (12), basal ganglia (17), and cerebellum (11). The thalamus (12) helps process information from the senses and transmit sensory data to other parts of the brain and includes various structures such as, but not limited to, the ventral posterolateral nucleus, ventral posteromedial nucleus, primary somatosensory cortex, and internal capsule. The basal ganglia (17) includes various groups of cerebral nuclei that play a role in the control and production of movement. Exemplary structures of the basal ganglia (17) include, but are not limited to, the striatum, subthalamic nucleus, and substantia nigra.

Figure 1C:
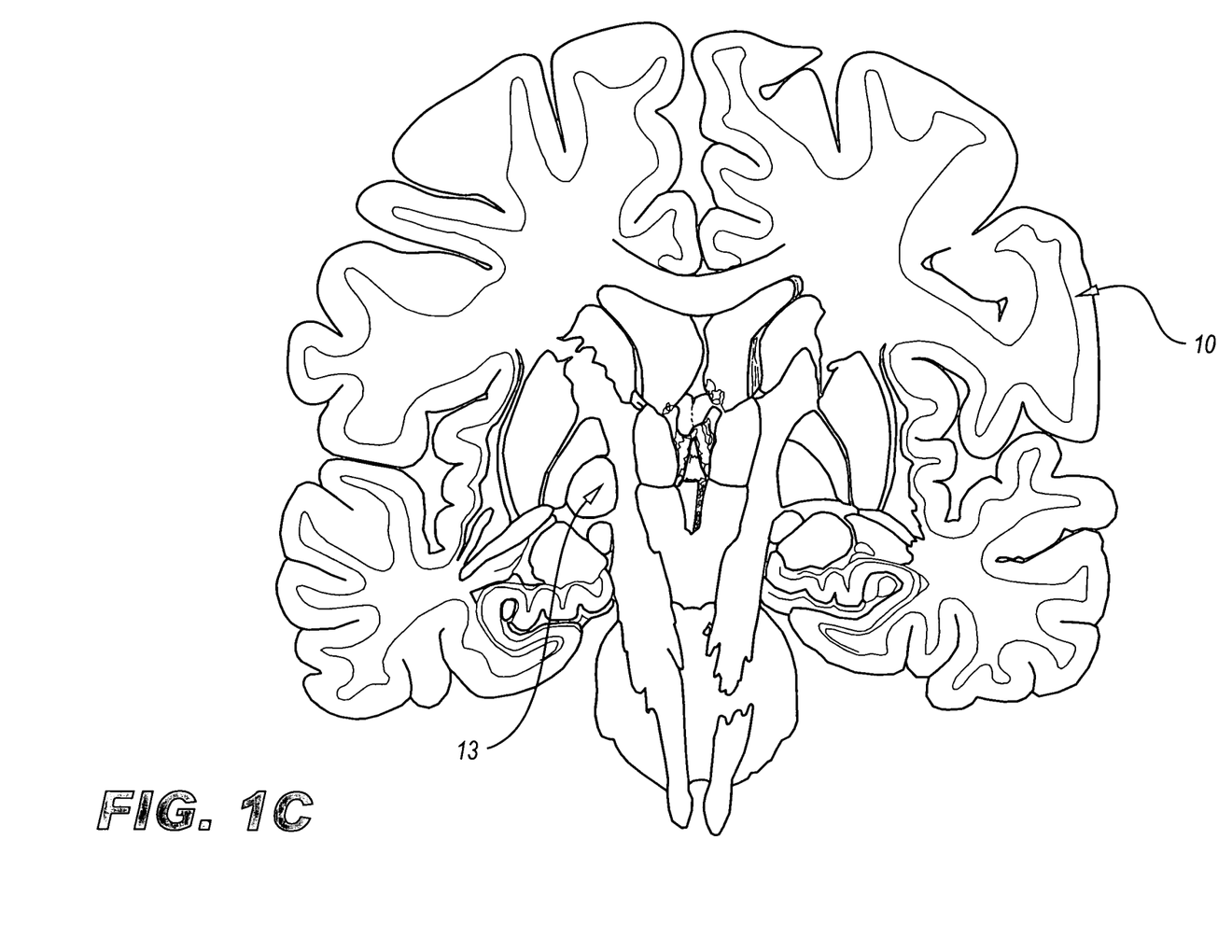
FIG. 1C is a coronal section view of the brain taken along the line indicated in FIG. 1B.

FIG. 1C is a coronal section view of the brain taken along the line indicated in FIG. 1B. FIG. 1C shows the globus pallidus (13), which is an area of the brain that affects movement, balance, and walking. The motor cortex (10) is also shown in FIG. 1C.

As mentioned, those who survive a stroke often suffer from a number of post-stroke disorders or sequelae. Exemplary post-stroke disorders include, but are not limited to, nerve cell death, pain, nervous disorders (e.g., chorea), movement disorders, motor weakness, paralysis, numbness, pressure sores, pneumonia, incontinence, coma, apraxia, appetite loss, vision loss, emotional disorders, and depression. As used herein, and in the appended claims, unless otherwise specifically denoted, the term "post-stroke disorder" will be used to refer to any disorder or sequela caused or influenced by a stroke.

Many areas of the brain have been implicated in post-stroke disorders. However, studies have shown that the motor cortex, thalamus, cerebellum, basal ganglia, globus pallidus, and/or periaqueductal gray are most likely to be primarily responsible for post-stroke disorders. It is believed that applying a stimulus to one or more of these areas of the brain may be useful in treating one or more post-stroke disorders. Consequently, as will be described in more detail below, a stimulator may be implanted in a patient who has suffered a stroke and configured to deliver a stimulus to one or more stimulation sites within the patient to treat one or more post-stroke disorders. The stimulus may include an electrical stimulation current, one or more drugs or other chemical stimulation, thermal stimulation, electromagnetic stimulation, mechanical stimulation, and/or any other suitable stimulation.

As used herein, and in the appended claims, the term "stimulator" will be used broadly to refer to any device that delivers a stimulus, such as an electrical stimulation current, one or more drugs or other chemical stimulation, thermal stimulation, electromagnetic stimulation, mechanical stimulation, and/or any other suitable stimulation at a stimulation site to treat a post-stroke disorder. Thus, the term "stimulator" includes, but is not limited to, a stimulator, microstimulator, implantable pulse generator (IPG), system control unit, spinal cord stimulator, cochlear implant, deep brain stimulator, drug pump, or similar device.

The stimulation site referred to herein may include any area that has been affected by a stroke and that is responsible for, or contributes to, a post-stroke disorder. For example, the stimulation site may include one or more of the following locations within the brain: the motor cortex, thalamus, cerebellum, basal ganglia, globus pallidus, and periaqueductal gray. As used herein, and in the appended claims, the term "motor cortex" will be used to refer to the primary motor cortex, premotor cortex, and supplementary motor cortex. The term "thalamus" will be used to refer to any structure of the thalamus, including, but not limited to, the ventral posterolateral nucleus and the ventral posteromedial nucleus. The term "cerebellum" will be used to refer to any structure of the cerebellum, including, but not limited to, the superior, middle and/inferior cerebellar peduncles.

It will be recognized that the stimulator may additionally or alternatively be configured to apply a stimulus to any nerve that innervates one of the stimulation sites, any blood vessel that supplies one of the stimulation sites, and/or any other tissue associated with the stimulation sites. Hence, as used herein and in the appended claims, unless otherwise specifically denoted, the term "stimulation site" will be used to refer to one or more of the above mentioned stimulation sites the brain and/or a nerve, blood vessel, or any other tissue associated with the above mentioned stimulation sites.

Figure 2:
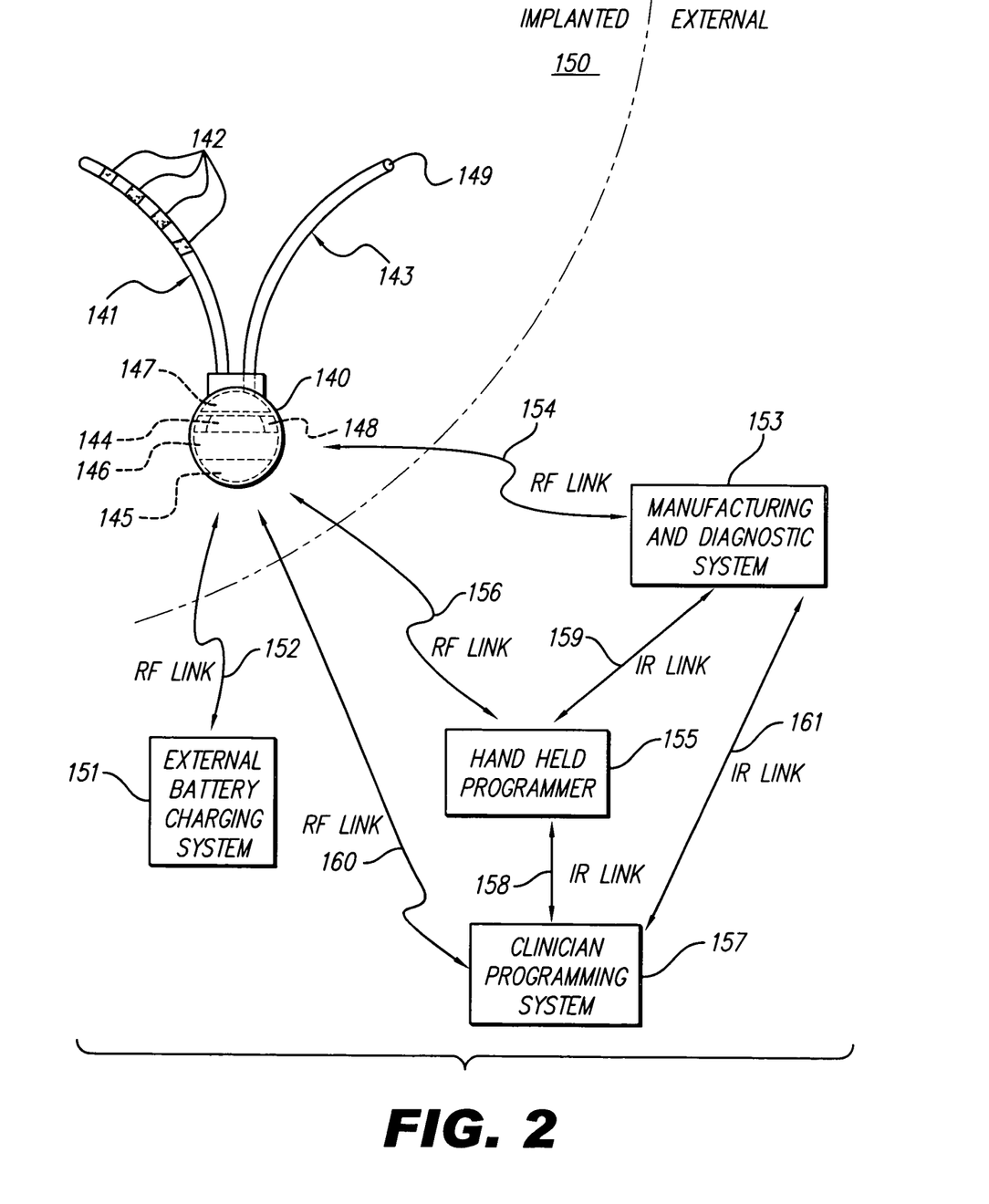
FIG. 2 illustrates an exemplary stimulator that may be used to apply a stimulus to a stimulation site within the brain of a patient to treat a post-stroke disorder according to principles described herein.

To facilitate an understanding of the methods of optimally treating a post-stroke disorder, a more detailed description of the stimulator and its operation will now be given with reference to the figures. FIG. 2 illustrates an exemplary stimulator (140) that may be implanted within a patient (150) and used to apply a stimulus to a stimulation site, e.g., an electrical stimulation of the stimulation site, an infusion of one or more drugs at the stimulation site, or both. The electrical stimulation function of the stimulator (140) will be described first, followed by an explanation of the possible drug delivery function of the stimulator (140). It will be understood, however, that the stimulator (140) may be configured to provide only electrical stimulation, only a drug stimulation, both types of stimulation or any other type of stimulation as best suits a particular patient.

The exemplary stimulator (140) shown in FIG. 2 is configured to provide electrical stimulation to a stimulation site within a patient and may include a lead (141) having a proximal end coupled to the body of the stimulator (140). The lead (141) also includes a number of electrodes (142) configured to apply an electrical stimulation current to a stimulation site. The lead (141) may include any number of electrodes (142) as best serves a particular application. The electrodes (142) may be arranged as an array, for example, having at least two or at least four collinear electrodes. In some embodiments, the electrodes are alternatively inductively coupled to the stimulator (140). The lead (141) may be thin (e.g., less than 3 millimeters in diameter) such that the lead (141) may be positioned near a stimulation site. In some alternative examples, as will be illustrated in connection with FIG. 3, the stimulator (140) is leadless.

As illustrated in FIG. 2, the stimulator (140) includes a number of components. It will be recognized that the stimulator (140) may include additional and/or alternative components as best serves a particular application. A power source (145) is configured to output voltage used to supply the various components within the stimulator (140) with power and/or to generate the power used for electrical stimulation. The power source (145) may be a primary battery, a rechargeable battery, super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like. Alternatively, the stimulator (140) may include one or more components configured to receive power from another medical device that is implanted within the patient.

When the power source (145) is a battery, it may be a lithium-ion battery or other suitable type of battery. When the power source (145) is a rechargeable battery, it may be recharged from an external system through a power link such as a radio frequency (RF) power link. One type of rechargeable battery that may be used is described in International Publication WO 01/82398 A1, published Nov. 1, 2001, and/or WO 03/005465 A1, published Jan. 16, 2003, both of which are incorporated herein by reference in their respective entireties. Other battery construction techniques that may be used to make a power source (145) include those shown, e.g., in U.S. Pat. Nos. 6,280,873; 6,458,171, and U.S. Publications 2001/0046625 A1 and 2001/0053476 A1, all of which are incorporated herein by reference in their respective entireties. Recharging can be performed using an external charger.

The stimulator (140) may also include a coil (148) configured to receive and/or emit a magnetic field (also referred to as a radio frequency (RF) field) that is used to communicate with, or receive power from, one or more external devices (151, 153, 155). Such communication and/or power transfer may include, but is not limited to, transcutaneously receiving data from the external device, transmitting data to the external device, and/or receiving power used to recharge the power source (145).

For example, an external battery charging system (EBCS) (151) may provide power used to recharge the power source (145) via an RF link (152). External devices including, but not limited to, a hand held programmer (HHP) (155), clinician programming system (CPS) (157), and/or a manufacturing and diagnostic system (MDS) (153) may be configured to activate, deactivate, program, and test the stimulator (140) via one or more RF links (154, 156). It will be recognized that the links, which are RF links (152, 154, 156) in the illustrated example, may be any type of link used to transmit data or energy, such as an optical link, a thermal link, or any other energy-coupling link. One or more of these external devices (153, 155, 157) may also be used to control the infusion of one or more drugs into the stimulation site.

Additionally, if multiple external devices are used in the treatment of a patient, there may be some communication among those external devices, as well as with the implanted stimulator (140). Again, any type of link for transmitting data or energy may be used among the various devices illustrated. For example, the CPS (157) may communicate with the HHP (155) via an infrared (IR) link (158), with the MDS (153) via an IR link (161), and/or directly with the stimulator (140) via an RF link (160). As indicated, these communication links (158, 161, 160) are not necessarily limited to IR and RF links and may include any other type of communication link. Likewise, the MDS (153) may communicate with the HHP (155) via an IR link (159) or via any other suitable communication link.

The HHP (155), MDS (153), CPS (157), and EBCS (151) are merely illustrative of the many different external devices that may be used in connection with the stimulator (140). Furthermore, it will be recognized that the functions performed by any two or more of the HHP (155), MDS (153), CPS (157), and EBCS (151) may be performed by a single external device. One or more of the external devices (153, 155, 157) may be embedded in a seat cushion, mattress cover, pillow, garment, belt, strap, pouch, or the like so as to be positioned near the implanted stimulator (140) when in use.

The stimulator (140) may also include electrical circuitry (144) configured to produce electrical stimulation pulses that are delivered to the stimulation site via the electrodes (142). In some embodiments, the stimulator (140) may be configured to produce monopolar stimulation. The stimulator (140) may alternatively or additionally be configured to produce multipolar stimulation including, but not limited to, bipolar or tripolar stimulation.

The electrical circuitry (144) may include one or more processors configured to decode stimulation parameters and generate the stimulation pulses. In some embodiments, the stimulator (140) has at least four channels and drives up to sixteen electrodes or more. The electrical circuitry (144) may include additional circuitry such as capacitors, integrated circuits, resistors, coils, and the like configured to perform a variety of functions as best serves a particular application.

The stimulator (140) may also include a programmable memory unit (146) for storing one or more sets of data and/or stimulation parameters. The stimulation parameters may include, but are not limited to, electrical stimulation parameters, drug stimulation parameters, and other types of stimulation parameters. The programmable memory (146) allows a patient, clinician, or other user of the stimulator (140) to adjust the stimulation parameters such that the stimulation applied by the stimulator (140) is safe and efficacious for treatment of a particular patient. The different types of stimulation parameters (e.g., electrical stimulation parameters and drug stimulation parameters) may be controlled independently. However, in some instances, the different types of stimulation parameters are coupled. For example, electrical stimulation may be programmed to occur only during drug stimulation or vice versa. Alternatively, the different types of stimulation may be applied at different times or with only some overlap. The programmable memory (146) may be any type of memory unit such as, but not limited to, random access memory (RAM), static RAM (SRAM), a hard drive, or the like.

The electrical stimulation parameters may control various parameters of the stimulation current applied to a stimulation site including, but not limited to, the frequency, pulse width, amplitude, electrode configuration (i.e., anode-cathode assignment), wave form (e.g., square or sinusoidal wave), burst pattern (e.g., burst on time and burst off time), duty cycle or burst repeat interval, ramp on time, and ramp off time of the stimulation current that is applied to the stimulation site. The drug stimulation parameters may control various parameters including, but not limited to, the amount of drugs infused at the stimulation site, the rate of drug infusion, and the frequency of drug infusion. For example, the drug stimulation parameters may cause the drug infusion rate to be intermittent, constant, or bolus. Other stimulation parameters that characterize other classes of stimuli are possible. For example, when tissue is stimulated using electromagnetic radiation, the stimulation parameters may characterize the intensity, wavelength, and timing of the electromagnetic radiation stimuli. When tissue is stimulated using mechanical stimuli, the stimulation parameters may characterize the pressure, displacement, frequency, and timing of the mechanical stimuli.

Specific stimulation parameters may have different effects on different post-stroke disorders and/or different patients. Thus, in some embodiments, the stimulation parameters may be adjusted by the patient, a clinician, or other user of the stimulator (140) as best serves the particular post-stroke disorder being treated. The stimulation parameters may also be automatically adjusted by the stimulator (140), as will be described below. For example, the stimulator (140) may increase excitement of a stimulation site by applying a stimulation current having a relatively low frequency (e.g., less than 100 Hz). The stimulator (140) may also decrease excitement of a stimulation site by applying a relatively high frequency (e.g., greater than 100 Hz). The stimulator (140) may also, or alternatively, be programmed to apply the stimulation current to a stimulation site intermittently or continuously.

Additionally, the exemplary stimulator (140) shown in FIG. 2 is configured to provide drug stimulation to a stroke patient by applying one or more drugs at a stimulation site within the patient to treat a post-stroke disorder. For this purpose, a pump (147) may also be included within the stimulator (140). The pump (147) is configured to store and dispense one or more drugs, for example, through a catheter (143). The catheter (143) is coupled at a proximal end to the stimulator (140) and may have an infusion outlet (149) for infusing dosages of the one or more drugs at the stimulation site. In some embodiments, the stimulator (140) may include multiple catheters (143) and/or pumps (147) for storing and infusing dosages of the one or more drugs at the stimulation site.

The pump (147) or controlled drug release device described herein may include any of a variety of different drug delivery systems. Controlled drug release devices based upon a mechanical or electromechanical infusion pump may be used. In other examples, the controlled drug release device can include a diffusion-based delivery system, e.g., erosion-based delivery systems (e.g., polymer-impregnated with drug placed within a drug-impermeable reservoir in communication with the drug delivery conduit of a catheter), electrodiffusion systems, and the like. Another example is a convective drug delivery system, e.g., systems based upon electroosmosis, vapor pressure pumps, electrolytic pumps, effervescent pumps, piezoelectric pumps and osmotic pumps. Another example is a micro-drug pump.

Exemplary pumps (147) or controlled drug release devices suitable for use as described herein include, but are not necessarily limited to, those disclosed in U.S. Pat. Nos. 3,760, 984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,360,019; 4,487,603; 4,627,850; 4,692,147; 4,725,852; 4,865,845; 5,057,318; 5,059,423; 5,112,614; 5,137,727; 5,234,692; 5,234,693; 5,728,396; 6,368,315 and the like. Additional exemplary drug pumps suitable for use as described herein include, but are not necessarily limited to, those disclosed in U.S. Pat. Nos. 4,562,751; 4,678,408; 4,685,903; 5,080,653; 5,097,122; 6,740,072; and 6,770,067. Exemplary micro-drug pumps suitable for use as described herein include, but are not necessarily limited to, those disclosed in U.S. Pat. Nos. 5,234, 692; 5,234,693; 5,728,396; 6,368,315; 6,666,845; and 6,620, 151. All of these listed patents are incorporated herein by reference in their respective entireties.

The one or more drugs that may be applied to a stimulation site to treat a post-stroke disorder may have an excitatory effect on the stimulation site. Additionally or alternatively, the one or more drugs may have an inhibitory effect on the stimulation site to treat the post-stroke disorder. Exemplary excitatory drugs that may be applied to a stimulation site to treat a post-stroke disorder include, but are not limited to, at least one or more of the following: an excitatory neurotransmitter (e.g., glutamate, dopamine, norepinephrine, epinephrine, acetylcholine, serotonin); an excitatory neurotransmitter agonist (e.g., glutamate receptor agonist, L-aspartic acid, N-methyl-D-aspartic acid (NMDA), bethanechol, norepinephrine); an inhibitory neurotransmitter antagonist(s) (e.g., bicuculline); an agent that increases the level of an excitatory neurotransmitter (e.g., edrophonium, Mestinon); and/or an agent that decreases the level of an inhibitory neurotransmitter (e.g., bicuculline).

Exemplary inhibitory drugs that may be applied to a stimulation site to treat a post-stroke disorder include, but are not limited to, at least one or more of the following: an inhibitory neurotransmitter(s) (e.g., gamma-aminobutyric acid, a.k.a. GABA, dopamine, glycine); an agonist of an inhibitory neurotransmitter (e.g., a GABA receptor agonist such as midazolam or clondine, muscimol); an excitatory neurotransmitter antagonist(s) (e.g. prazosin, metoprolol, atropine, benztropine); an agent that increases the level of an inhibitory neurotransmitter; an agent that decreases the level of an excitatory neurotransmitter (e.g., acetylcholinesterase, Group II metabotropic glutamate receptor (mGluR) agonists such as DCG-IV); a local anesthetic agent (e.g., lidocaine); and/or an analgesic medication. It will be understood that some of these drugs, such as dopamine, may act as excitatory neurotransmitters in some stimulation sites and circumstances, and as inhibitory neurotransmitters in other stimulation sites and circumstances.

Additional or alternative drugs that may be applied to a stimulation site to treat a post-stroke disorder include at least one or more of the following substances: one or more heat shock proteins (e.g., HSP72), proteasome inhibitors (e.g., PS-341), COX-2 inhibitors, matrix metalloproteinase inhibitors, recombinant tissue plasminogen activators (e.g., rt-PA, BCL-2), immunomodulators (e.g., broad-spectrum chemokine inhibitor, NR58.3.14.3, cyclosporin A, N-methyl-val-4- cyclosporin A), neurotrophic factors (e.g., glial cell line-derived neurotrophic factors (GDNF), brain-derived neurotrophic factors (BDNF)), and gene carrying viruses (e.g., delivery of a drug, e.g., BCL-2, with a virus such as herpes simplex virus (HSV) or recombinant adeno-associated virus (rAAV).

Any of the drugs listed above, alone or in combination, or other drugs or combinations of drugs developed or shown to treat a post-stroke disorder may be applied to the stimulation site to treat the post-stroke disorder. As used herein and in the appended claims, "treating" a post-stroke disorder refers to any amelioration of either the cause or symptoms of a post-stroke disorder. In some embodiments, the one or more drugs are infused chronically into the stimulation site. Additionally or alternatively, the one or more drugs may be infused acutely into the stimulation site in response to a biological signal or a sensed need for the one or more drugs.

The stimulator (140) of FIG. 2 is illustrative of many types of stimulators that may be used to apply a stimulus to a stimulation site to treat a post-stroke disorder. For example, the stimulator (140) may include an implantable pulse generator (IPG) coupled to one or more leads having a number of electrodes, a spinal cord stimulator (SCS), a cochlear implant, a deep brain stimulator, a drug pump (mentioned previously), a micro-drug pump (mentioned previously), or any other type of implantable stimulator configured to deliver a stimulus at a stimulation site within a patient. Exemplary IPGs suitable for use as described herein include, but are not limited to, those disclosed in U.S. Pat. Nos. 6,381,496, 6,553,263; and 6,760,626. Exemplary spinal cord stimulators suitable for use as described herein include, but are not limited to, those disclosed in U.S. Pat. Nos. 5,501,703; 6,487,446; and 6,516,227. Exemplary cochlear implants suitable for use as described herein include, but are not limited to, those disclosed in U.S. Pat. Nos. 6,219,580; 6,272,382; and 6,308,101. Exemplary deep brain stimulators suitable for use as described herein include, but are not limited to, those disclosed in U.S. Pat. Nos. 5,938,688; 6,016,449; and 6,539,263. All of these listed patents are incorporated herein by reference in their respective entireties.

Alternatively, the stimulator (140) may include an implantable microstimulator, such as a BION® microstimulator (Advanced Bionics® Corporation, Valencia, Calif.). Various details associated with the manufacture, operation, and use of implantable microstimulators are disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

Figure 3:
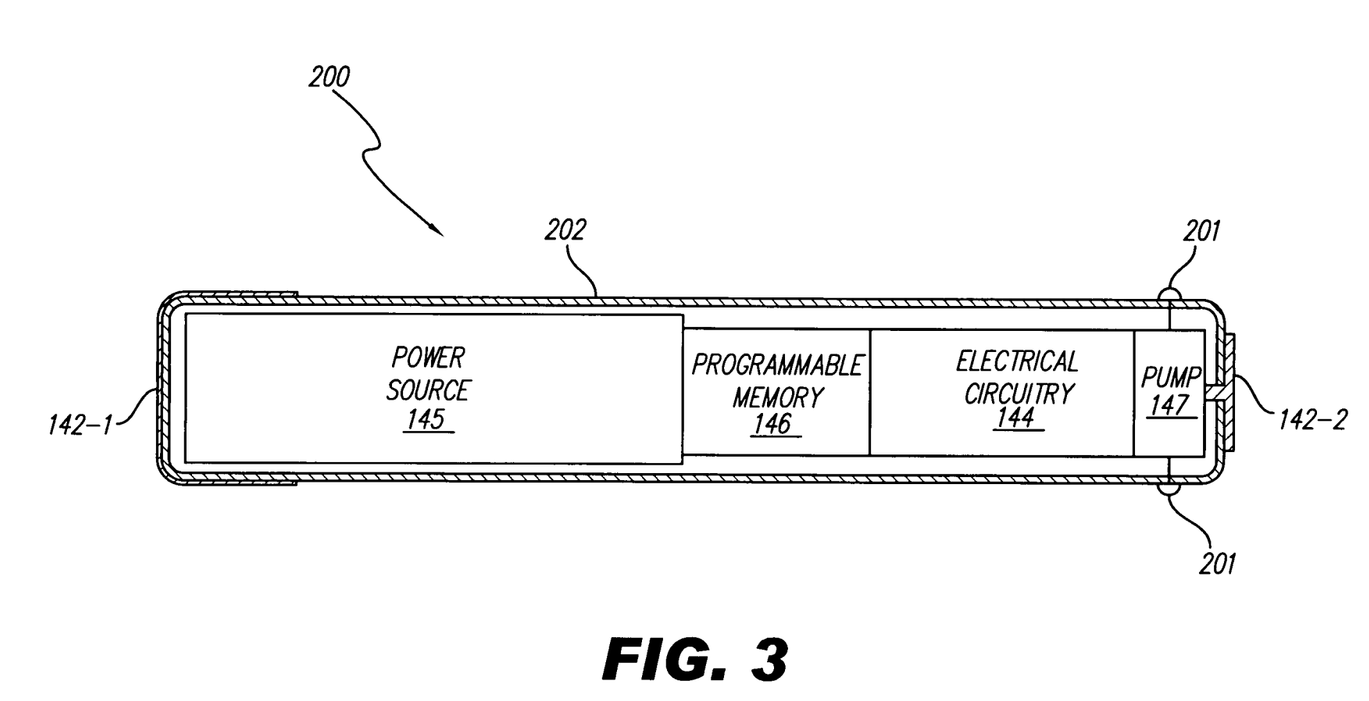
FIG. 3 illustrates an exemplary microstimulator that may be used as the stimulator according to principles described herein.

FIG. 3 illustrates an exemplary microstimulator (200) that may be used as the stimulator (140; FIG. 2) described herein. Other configurations of the microstimulator (200) are possible, as shown in the above-referenced patents and as described further below.

As shown in FIG. 3, the microstimulator (200) may include the power source (145), the programmable memory (146), the electrical circuitry (144), and the pump (147) described in connection with FIG. 2. These components are housed within a capsule (202). The capsule (202) may be a thin, elongated cylinder or any other shape as best serves a particular application. The shape of the capsule (202) may be determined by the structure of the desired target nerve, the surrounding area, and the method of implantation. In some embodiments, the volume of the capsule (202) is substantially equal to or less than three cubic centimeters. In some embodiments, the microstimulator (200) may include two or more leadless electrodes (142) disposed on the outer surface of the microstimulator (200).

The external surfaces of the microstimulator (200) may advantageously be composed of biocompatible materials. For example, the capsule (202) may be made of glass, ceramic, metal, or any other material that provides a hermetic package that will exclude water vapor but permit passage of electromagnetic fields used to transmit data and/or power. The electrodes (142) may be made of a noble or refractory metal or compound, such as platinum, iridium, tantalum, titanium, titanium nitride, niobium or alloys of any of these, in order to avoid corrosion or electrolysis which could damage the surrounding tissues and the device.

The microstimulator (200) may also include one or more infusion outlets (201). The infusion outlets (201) facilitate the infusion of one or more drugs at a stimulation site to treat a post-stroke disorder. The infusion outlets (201) may dispense one or more drugs directly to the treatment site. Alternatively, catheters may be coupled to the infusion outlets (201) to deliver the drug therapy to a stimulation site some distance from the body of the microstimulator (200). The stimulator (200) of FIG. 3 also includes electrodes (142-1 and 142-2) at either end of the capsule (202). One of the electrodes (142) may be designated as a stimulating electrode to be placed close to the treatment site and one of the electrodes (142) may be designated as an indifferent electrode used to complete a stimulation circuit.

The microstimulator (200) may be implanted within a patient with a surgical tool such as a hypodermic needle, bore needle, or any other tool specially designed for the purpose. Alternatively, the microstimulator (200) may be implanted using endoscopic or laparoscopic techniques.

Figure 4:
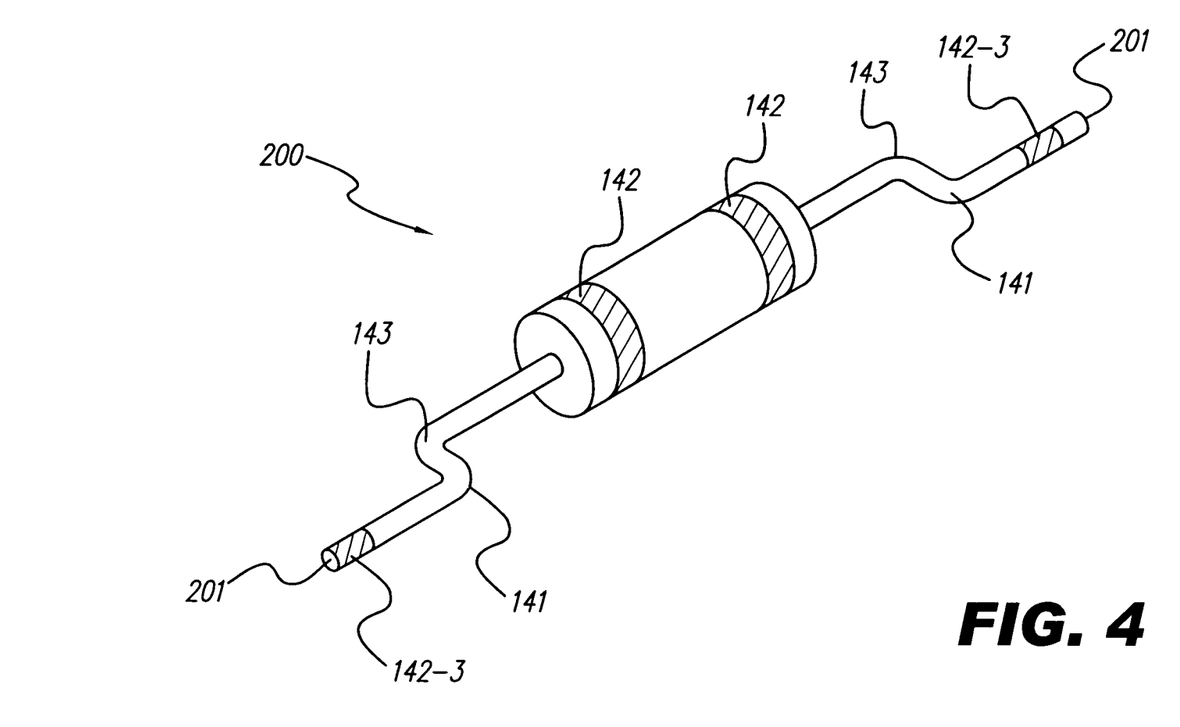
FIG. 4 shows one or more catheters coupled to a microstimulator according to principles described herein.

FIG. 4 shows an example of a microstimulator (200) with one or more catheters (143) coupled to the infusion outlets on the body of the microstimulator (200). With the catheters (143) in place, the infusion outlets (201) that actually deliver the drug therapy to target tissue are located at the ends of catheters (143). Thus, in the example of FIG. 4, a drug therapy is expelled by the pump (147, FIG. 3) from an infusion outlet (201, FIG. 3) in the casing (202, FIG. 3) of the microstimulator (200), through the catheter (143), out an infusion outlet (201) at the end of the catheter (143) to the stimulation site within the patient. As shown in FIG. 4, the catheters (143) may also serve as leads (141) having one or more electrodes (142-3) disposed thereon. Thus, the catheters (143) and leads (141) of FIG. 4 permit infused drugs and/or electrical stimulation current to be directed to a stimulation site while allowing most elements of the microstimulator (200) to be located in a more surgically convenient site. The example of FIG. 4 may also include leadless electrodes (142) disposed on the housing of the microstimulator (200), in the same manner described above.

Figure 5:
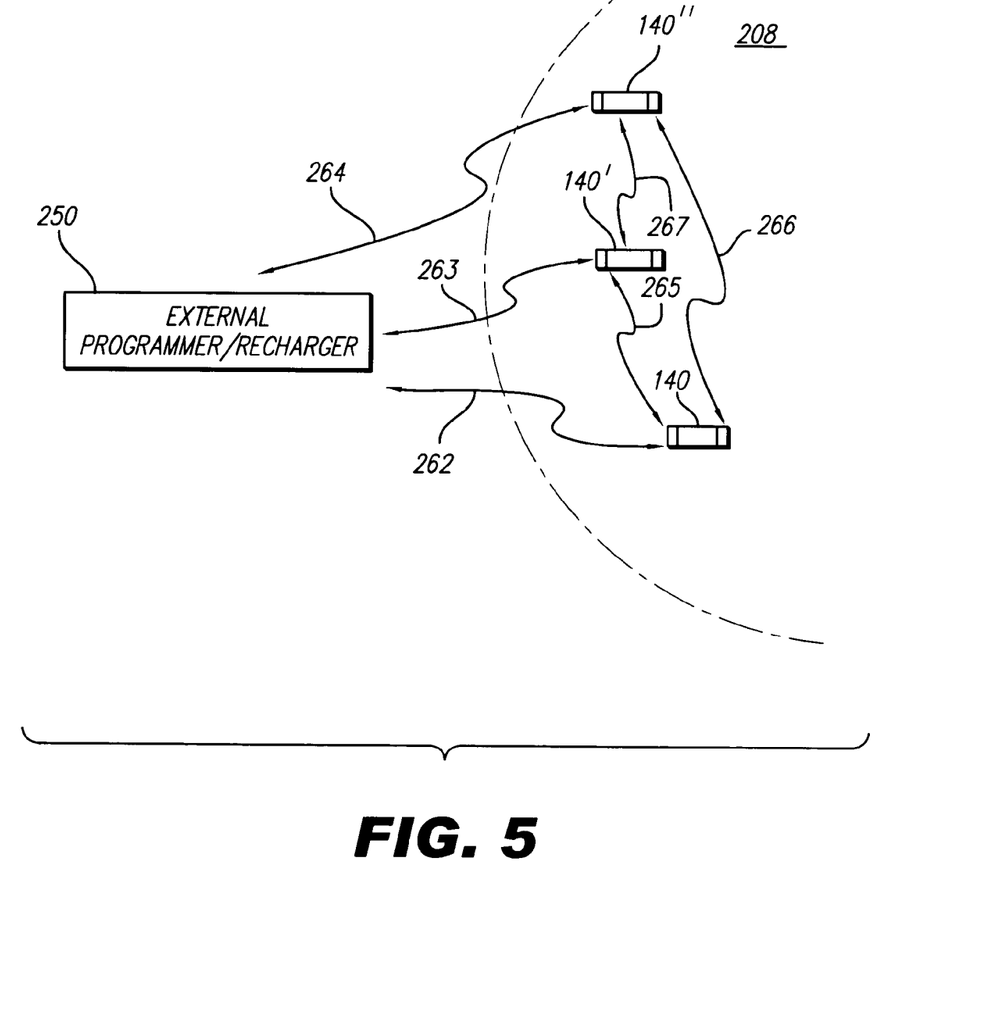
FIG. 5 depicts a number of stimulators configured to communicate with each other and/or with one or more external devices according to principles described herein.

Returning to FIG. 2, the stimulator (140) may be configured to operate independently. Alternatively, as shown in FIG. 5 and described in more detail below, the stimulator (140) may be configured to operate in a coordinated manner with one or more additional stimulators, other implanted devices, or other devices external to the patient's body. For instance, a first stimulator may control, or operate under the control of, a second stimulator, other implanted device, or other device external to the patient's body. The stimulator (140) may be configured to communicate with other implanted stimulators, other implanted devices, or other devices external to the patient's body via an RF link, an untrasonic link, an optical link, or any other type of communication link. For example, the stimulator (140) may be configured to communicate with an external remote control unit that is capable of sending commands and/or data to the stimulator (140) and that is configured to receive commands and/or data from the stimulator (140).

In order to determine the strength and/or duration of electrical stimulation and/or amount and/or type(s) of stimulating drug(s) required to most effectively treat a post-stroke disorder, various indicators of a post-stroke disorder and/or a patient's response to treatment may be sensed or measured. These indicators include, but are not limited to, electrical activity of the brain (e.g., EEG); discharge frequency of a neural population in the brain; nerve activity (e.g., electroneurography (ENG)); muscle activity (e.g., limb electromyography (EMG)); head or limb movement or acceleration; neurotransmitter levels; hormone levels; dopamine levels; interleukin levels; cytokine levels; lymphokine levels; chemokine levels; growth factor levels; electrolyte levels; enzyme levels; metabolic activity in the brain; blood flow rate in the head, neck or other areas of the body; medication levels within the patient; temperature of tissue at the stimulation site; physical activity level, e.g., based on accelerometer recordings; and/or brain hyperexcitability, e.g., increased response of given tissue to the same input. In some embodiments, the stimulator (140) may be configured to adjust the stimulation parameters in a closed loop manner in response to these measurements. The stimulator (140) may be configured to perform the measurements. Alternatively, other sensing devices may be configured to perform the measurements and transmit the measured values to the stimulator (140). Exemplary sensing devices include, but are not limited to, chemical sensors, deep brain sensing leads, electrodes, optical sensors, mechanical (e.g., motion, pressure) sensors, temperature sensors, and Chemically Sensitive Field-Effect Transistors (CHEMFETs) (e.g., Enzyme-Selective Field-Effect Transistors (ENFETs), Ion-Sensitive Field-Effect Transistors).

For instance, one or more stimulators or other recording devices may be used to record neural activity of a stimulation site in order to determine the discharge frequency of the neural population in that stimulation site. The stimulation parameters may then be adjusted in response to the sensed neural activity. For example, the amplitude of the stimulation current may be increased if the discharge frequency is above a programmable threshold frequency (e.g., 50 Hz). The amplitude of the stimulation current may be decreased if the discharge frequency is less than another programmable threshold frequency (e.g., 2 Hz). It will be recognized that the threshold frequencies may vary as best serves a particular application.

In another example, for post-stroke disorder patients with chorea (a nervous disorder that can result in spasmodic movements), one or more accelerometers may be used to sense spatial orientation, motion, and/or acceleration of brain tissue. It is believed that the amplitude of rhythmic brain tissue acceleration may be an indicator of the amplitude of chorea. Hence, the amplitude of the stimulation current may be increased if the amplitude of rhythmic brain tissue acceleration is above a programmable threshold. Likewise, the amplitude of the stimulation current may be decreased if the amplitude of rhythmic brain tissue acceleration is below a programmable threshold. One or more accelerometers may additionally or alternatively be used to sense spatial orientation, motion, and/or acceleration of limbs or other extremities.

Thus, one or more external devices may be provided to interact with the stimulator (140), and may be used to accomplish at least one or more of the following functions:

Function 1: If necessary, transmit electrical power to the stimulator (140) in order to power the stimulator (140) and/or recharge the power source (145).

Function 2: Transmit data to the stimulator (140) in order to change the stimulation parameters used by the stimulator (140).

Function 3: Receive data indicating the state of the stimulator (140) (e.g., battery level, drug level, stimulation parameters, etc.).

Additional functions may include adjusting the stimulation parameters based on information sensed by the stimulator (140) or by other sensing devices.

By way of example, an exemplary method of treating a post-stroke disorder may be carried out according to the following sequence of procedures. The steps listed below may be modified, reordered, and/or added to as best serves a particular application.

1. A stimulator (140) is implanted so that its electrodes (142) and/or infusion outlet (149) are coupled to or located near a stimulation site (e.g., the motor cortex).

2. The stimulator (140) is programmed to apply at least one stimulus to the stimulation site. The stimulus may include electrical stimulation, drug stimulation, chemical stimulation, thermal stimulation, electromagnetic stimulation, mechanical stimulation, and/or any other suitable stimulation.

3. When the patient desires to invoke stimulation, the patient sends a command to the stimulator (140) (e.g., via a remote control) such that the stimulator (140) delivers the prescribed stimulation. The stimulator (140) may be alternatively or additionally configured to automatically apply the stimulation in response to sensed indicators of the post-stroke disorder.

4. To cease stimulation, the patient may turn off the stimulator (140) (e.g., via a remote control).

5. Periodically, the power source (145) of the stimulator (140) is recharged, if necessary, in accordance with Function 1 described above. As will be described below, this recharging function can be made much more efficient using the principles disclosed herein.

In other examples, the treatment administered by the stimulator (140), i.e., drug therapy and/or electrical stimulation, may be automatic and not controlled or invoked by the patient.

For the treatment of different patients, it may be desirable to modify or adjust the algorithmic functions performed by the implanted and/or external components, as well as the surgical approaches. For example, in some situations, it may be desirable to employ more than one stimulator (140), each of which could be separately controlled by means of a digital address. Multiple channels and/or multiple patterns of stimulation may thereby be used to deal with multiple post-stroke disorders, such as, for example, the combination of a nervous disorder with an emotional disorder.

As shown in the example of FIG. 5, a first stimulator (140) implanted within the patient (208) provides a stimulus to a first location; a second stimulator (140') provides a stimulus to a second location; and a third stimulator (140") provides a stimulus to a third location. As mentioned earlier, the implanted devices may operate independently or may operate in a coordinated manner with other implanted devices or other devices external to the patient's body. That is, an external controller (250) may be configured to control the operation of each of the implanted devices (140, 140', and 140"). In some embodiments, an implanted device, e.g., stimulator (140), may control, or operate under the control of, another implanted device(s), e.g., stimulator (140') and/or stimulator (140"). Control lines (262-267) have been drawn in FIG. 5 to illustrate that the external controller (250) may communicate or provide power to any of the implanted devices (140, 140', and 140") and that each of the various implanted devices (140, 140', and 140") may communicate with and, in some instances, control any of the other implanted devices.

As a further example of multiple stimulators (140) operating in a coordinated manner, the first and second stimulators (140, 140') of FIG. 5 may be configured to sense various indicators of a post-stroke disorder and transmit the measured information to the third stimulator (140"). The third stimulator (140") may then use the measured information to adjust its stimulation parameters and apply stimulation to a stimulation site accordingly. The various implanted stimulators may, in any combination, sense indicators of a post-stroke disorder, communicate or receive data on such indicators, and adjust stimulation parameters accordingly.

Alternatively, the external device (250) or other external devices communicating with the external device may be configured to sense various indicators of a patient's condition. The sensed indicators can then be collected by the external device (250) for relay to one or more of the implanted stimulators or may be transmitted directly to one or more of the implanted stimulators by any of an array of external sensing devices. In either case, the stimulator, upon receiving the sensed indicator(s), may adjust stimulation parameters accordingly. In other examples, the external controller (250) may determine whether any change to stimulation parameters is needed based on the sensed indicators. The external device (250) may then signal a command to one or more of the stimulators to adjust stimulation parameters accordingly.

The stimulator (140) of FIG. 2 may be implanted within a stroke patient using any suitable surgical procedure such as, but not limited to, injection, small incision, open placement, laparoscopy, or endoscopy. Exemplary methods of implanting a microstimulator, for example, are described in U.S. Pat. Nos. 5,193,539; 5,193,540; 5,312,439; 6,185,452; 6,164,284; 6,208,894; and 6,051,017. Exemplary methods of implanting an SCS, for example, are described in U.S. Pat. Nos. 5,501, 703; 6,487,446; and 6,516,227. Exemplary methods of implanting a deep brain stimulator, for example, are described in U.S. Pat. Nos. 5,938,688; 6,016,449; and 6,539, 263. All of these listed patents are incorporated herein by reference in their respective entireties.

Figure 6:
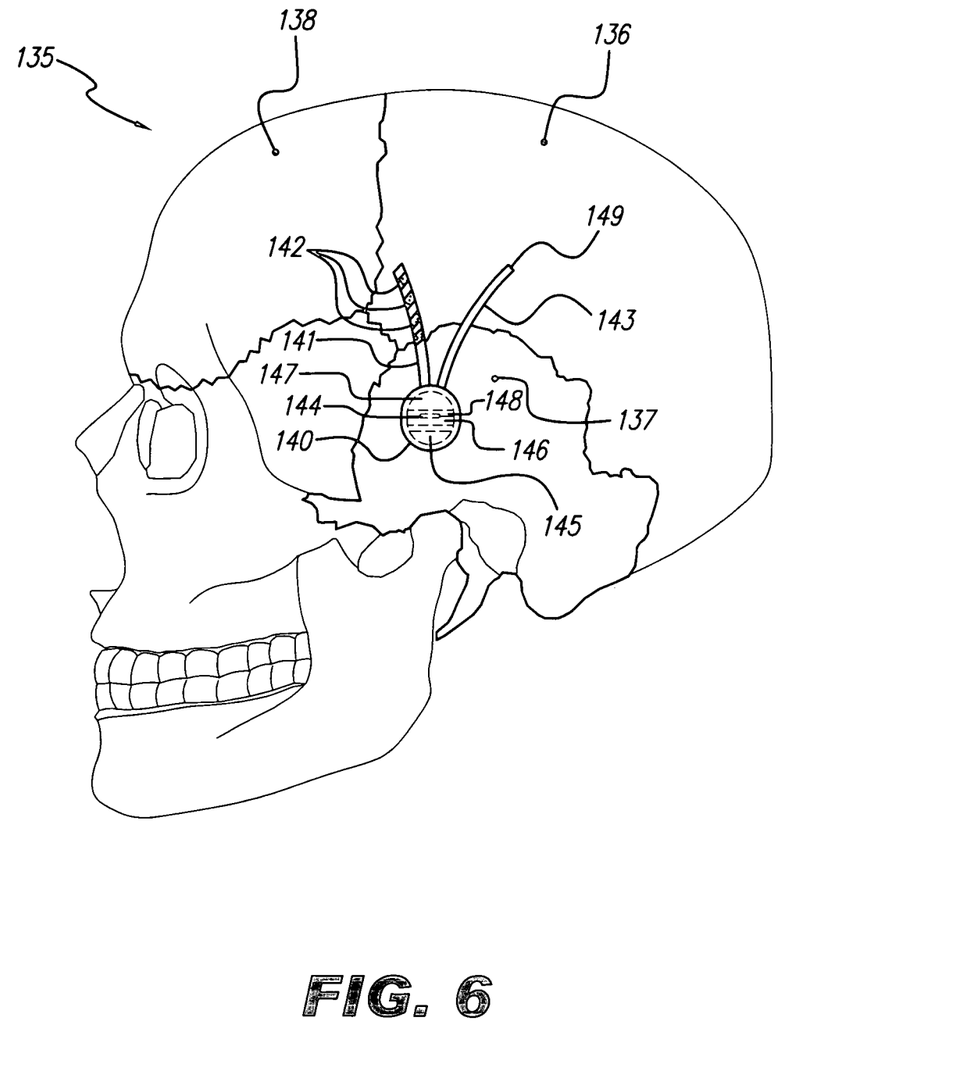
FIG. 6 illustrates a stimulator that has been implanted beneath the scalp of a patient to stimulate a stimulation site within the brain associated with a post-stroke disorder according to principles described herein.

By way of example, FIG. 6 shows a stimulator (140) (e.g., a deep brain stimulator) that has been implanted beneath the scalp of a patient to stimulate a stimulation site within the brain associated with a post-stroke disorder. The stimulator (140) may be implanted in a surgically-created shallow depression or opening in the skull (135). For instance, the depression may be made in the parietal bone (136), temporal bone (137), frontal bone (138), or any other bone within the skull (135) as best serves a particular application. The stimulator (140) may conform to the profile of surrounding tissue(s) and/or bone(s), thereby minimizing the pressure applied to the skin or scalp. Additionally or alternatively, the stimulator (140) may be implanted in a subdural space over any of the lobes of the brain or in an intracerebral ventricle.

In some embodiments, as shown in FIG. 6, a lead (141) and/or catheter (143) run subcutaneously to an opening in the skull (135) and pass through the opening such that it is in communication with a stimulation site in the brain. As used herein and in the appended claims, the term "in communication with" refers to the stimulator (140), lead (141), and/or catheter (143) being adjacent, in the general vicinity, in close proximity, directly next to, or directly on the stimulation site such that stimulation can be effectively delivered.

Figure 7:
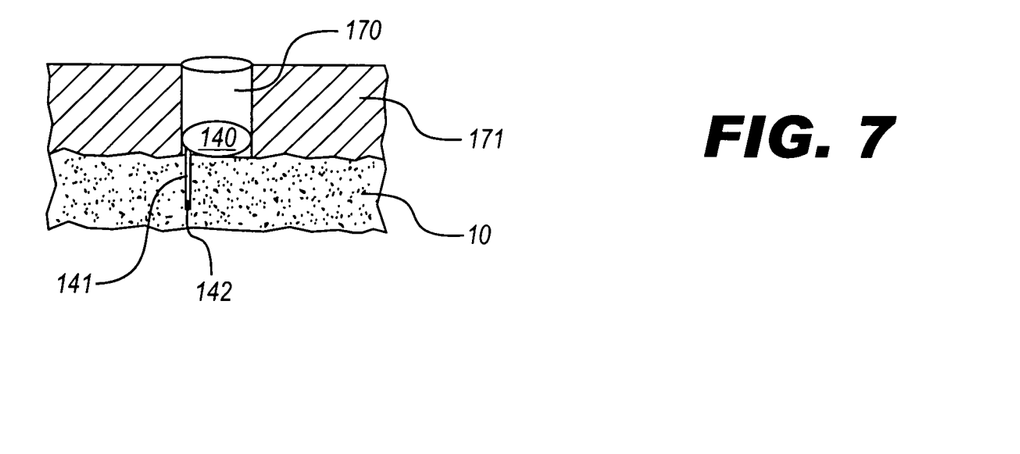
FIG. 7 is cross-sectional view of a stimulator implanted within a hole created in the skull of a stroke patient according to principles described herein.

Alternatively, as shown in the cross-sectional view of FIG. 7, the stimulator (140) may be implanted within the lumen of a hole (170) created in the skull (171) and configured to apply a stimulus to a stimulation site within the brain (e.g., the motor cortex (10)). The hole (170) may be a bun hole, for example, and may be created with a surgical drill or any other suitable device. The hole (170) extends at least partially into the skull (171), and, as shown in FIG. 7, may extend all the way through the skull (171). The stimulator (140) is placed within the lumen of the hole (170) and coupled to the walls of the hole (170) and/or the top surface of the stimulation site, e.g., the motor cortex (10), using an adhesive, suture, or any other fastening device. Once the stimulator (140) has been implanted, the hole (170) may be covered by an appropriately sized cap (not shown).

As shown in FIG. 7, a lead (141) may be coupled to the stimulator (140) with the distal end of the lead (141) being routed to a particular location within the motor cortex (10) or other stimulation site in the brain. The distal end of the lead (141) may include one or more electrodes (142) for delivering electrical stimulation to the stimulation site. As described and illustrated above, a catheter (not shown) may additionally or alternatively be coupled to the stimulator (140) and routed to the stimulation site so as to deliver one or more drugs at the stimulation site.

Figure 8A:
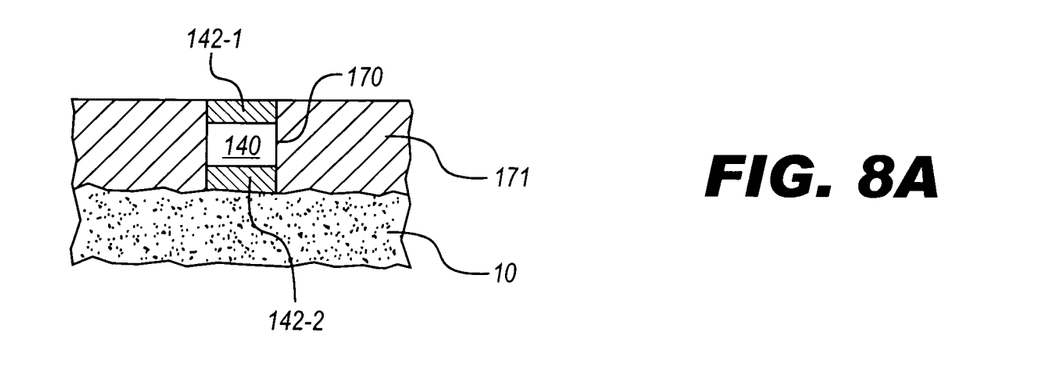
FIG. 8A is a cross-sectional view of a stimulator having two ring-like electrodes disposed on its surface implanted within a hole created in the skull of a stroke patient according to principles described herein.
Figure 8B:
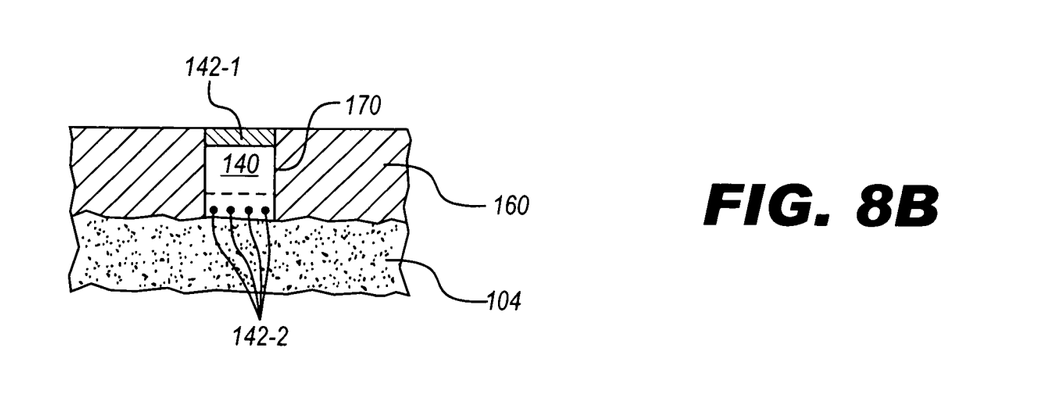
FIG. 8B is a cross-sectional view of a stimulator having multiple electrodes disposed thereon implanted within a hole created in the skull of a stroke patient according to principles described herein.

As mentioned, the stimulator (140) may be leadless. FIGS. 8A-8B are cross sectional views of exemplary leadless stimulators (140) that have been implanted within the lumen of a hole (170) created in the skull (171). In this manner, the stimulation site within the brain may be stimulated without having to physically invade the brain itself.

For example, FIG. 8A shows an exemplary stimulator (140) with two ring-like electrodes (142) disposed on its surface. The electrode (142-2) more proximal to the stimulation site, e.g., the motor cortex (10), may be configured to act as a stimulating electrode while the electrode (142-2) more distal to the stimulation site may be configured to act as the indifferent electrode.

FIG. 8B shows an alternative electrode arrangement wherein the end most proximal to the stimulation site includes multiple electrodes (142-2) disposed thereon. Each electrode (142-2) may be selectively configured to act as either an anode or cathode so that monopolar and/or multipolar stimulation may be applied to the stimulation site. The distal end of the stimulator (140) may also include a selectively programmable electrode (142).

It will be recognized that the stimulation site in the examples of FIGS. 7-8B is the motor cortex (10) for illustrative purposes only and that the stimulation site may additionally or alternatively include any of the other stimulation sites mentioned herein.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method of treating a post-stroke disorder, said method comprising: applying at least one stimulus to a periaqueductal gray within a patient with an implanted stimulator in accordance with one or more stimulation parameters to treat said post-stroke disorder, wherein said stimulator is at least partially disposed in a skull of said patient.

2. The method of claim 1, further comprising: implanting a lead having one or more electrodes disposed thereon in communication with said periaqueductal gray, wherein said stimulus comprises a stimulation current delivered via said electrodes.

3. The method of claim 1, further comprising sensing at least one indicator related to said post-stroke disorder and using said at least one sensed indicator to adjust one or more of said stimulation parameters.

4. The method of claim 3, wherein said at least one indicator comprises at least one or more of an electrical activity of a brain, a discharge frequency of a neural population in said brain, a nerve activity, a muscle activity, a movement of a head, a movement of a limb, a chemical level of said brain, a neurotransmitter level, a hormone level, a medication level, a dopamine level, an interleukin level, a cytokine level, a lymphokine level, a chemokine level, a growth factor level, an electrolyte level, and an enzyme level.

* * * * *